US010517982B2

(12) United States Patent
Vega et al.

(10) Patent No.: US 10,517,982 B2
(45) Date of Patent: Dec. 31, 2019

(54) ABSORBENT ARTICLE COMPRISING A LOTION COMPOSITION FOR REDUCING ADHERENCE OF FECES OR MENSES TO THE SKIN

(71) Applicant: The Procter & Gamble Company, Cincinnati, OH (US)

(72) Inventors: Victor Nicholas Vega, Cincinnati, OH (US); Rodrigo Rosati, Frankfurt am Main (DE); Cornelia Beate Martynus, Nidderau-Ostheim (DE); Randall Alan Watson, Loveland, OH (US); Brandon Ellis Wise, Cincinnati, OH (US); Thomas James Klofta, Cincinnati, OH (US); Donald Carroll Roe, West Chester, OH (US); Randall Glenn Marsh, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 769 days.

(21) Appl. No.: 15/162,721

(22) Filed: May 24, 2016

(65) Prior Publication Data

US 2016/0263273 A1 Sep. 15, 2016

(30) Foreign Application Priority Data

May 15, 2007 (EP) ..................................... 07108202

(51) Int. Cl.
| | |
|---|---|
| A61F 13/511 | (2006.01) |
| A61L 15/50 | (2006.01) |
| A61L 15/44 | (2006.01) |
| A61L 15/16 | (2006.01) |
| A61F 13/49 | (2006.01) |
| A61F 13/84 | (2006.01) |
| A61L 15/20 | (2006.01) |
| A61L 15/26 | (2006.01) |

(52) U.S. Cl.
CPC .......... *A61L 15/44* (2013.01); *A61F 13/4902* (2013.01); *A61F 13/51113* (2013.01); *A61F 13/8405* (2013.01); *A61L 15/16* (2013.01); *A61L 15/20* (2013.01); *A61L 15/26* (2013.01); *A61L 15/50* (2013.01); *A61F 2013/49092* (2013.01)

(58) Field of Classification Search
CPC ............ A61F 13/2074; A61F 13/51113; A61F 13/55145; A61F 13/5519; A61F 13/8405; A61F 2013/51066; A61F 2013/51073; A61F 2013/51117; A61F 2013/8455; A61F 2013/8461; A61L 15/44; A61L 15/50
See application file for complete search history.

(56) References Cited

U.S. PATENT DOCUMENTS

| | | | |
|---|---|---|---|
| 1,807,304 | A | 5/1931 | Calvert |
| 1,926,900 | A | 9/1933 | Haas |
| 1,946,911 | A | 2/1934 | Lindbergar et al. |
| 3,322,123 | A | 5/1967 | Griswold et al. |
| 3,489,148 | A | 1/1970 | Duncan et al. |
| 3,860,003 | A | 1/1975 | Buell |
| 4,253,461 | A | 3/1981 | Strickland et al. |
| 4,597,760 | A | 7/1986 | Buell |
| 4,597,761 | A | 7/1986 | Buell |
| 4,695,278 | A | 9/1987 | Lawson |
| 4,704,115 | A | 11/1987 | Buell |
| 4,738,676 | A | 4/1988 | Osborn, III |
| 4,738,678 | A | 4/1988 | Paulis |
| 4,795,454 | A | 1/1989 | Dragoo |
| 4,804,909 | A | 2/1989 | Fink |
| 4,808,178 | A | 2/1989 | Aziz et al. |
| 4,909,802 | A | 3/1990 | Ahr et al. |
| 4,964,860 | A | 10/1990 | Gipson et al. |
| 5,151,092 | A | 9/1992 | Buell et al. |
| 5,221,274 | A | 6/1993 | Buell et al. |
| 5,246,433 | A | 9/1993 | Hasse et al. |
| 5,261,531 | A | 11/1993 | Nieves |
| B149,648 | I5 | 1/1994 | Gipson et al. |
| 5,318,774 | A | 6/1994 | Alban et al. |
| 5,482,765 | A | 1/1996 | Bradley et al. |
| 5,525,346 | A | 6/1996 | Hartung et al. |
| 5,554,145 | A | 9/1996 | Roe et al. |

(Continued)

FOREIGN PATENT DOCUMENTS

| | | |
|---|---|---|
| CN | 1 555 274 A | 12/2004 |
| EP | 1371379 A1 | 12/2003 |

(Continued)

OTHER PUBLICATIONS

All Office Actions, U.S. Appl. No. 12/121,174.
EP Opinion for Application No. EP07108199.6, 3 pages.
EP Search Report for Application No. EP07108199.6, with Annex, 4 pages.
International Search Report, PCT/IB2008/051923, dated Aug. 13, 2008, 16 pages.
All Office Actions, U.S. Appl. No. 12/121,261.
All Office Actions, U.S. Appl. No. 11/946,631.
All Office Actions, U.S. Appl. No. 12/121,375.
PCT International Search Report, PCT/IB2008/051921 dated May 15, 2008.

*Primary Examiner* — Catharine L Anderson
(74) *Attorney, Agent, or Firm* — Daniel S. Albrecht; Christian M. Best; Wednesday G. Shipp

(57) ABSTRACT

An absorbent article, intended to be worn by a wearer, wherein at least a part of a body facing surface of that article has a lotion composition. The lotion composition includes at least one first compound which is liquid at 25° C. and at least one second compound which is solid at 25° C. The first compound is a liquid polyethylene glycol, and the second compound is a solid fatty compound selected from the group consisting of solid fatty acids, solid fatty alcohol and solid fatty soaps. When the solid fatty compound is a solid fatty acid, then the total amount of liquids is higher than the total amount of solids.

20 Claims, No Drawings

(56) References Cited

U.S. PATENT DOCUMENTS

| | | |
|---|---|---|
| 5,607,760 A | 3/1997 | Roe |
| 5,609,587 A | 3/1997 | Roe |
| 5,643,588 A | 7/1997 | Roe et al. |
| 5,762,644 A | 6/1998 | Osborn, III et al. |
| 5,827,917 A | 10/1998 | Fourty |
| 5,830,487 A | 11/1998 | Klofta et al. |
| D404,814 S | 1/1999 | Mayer |
| 5,965,508 A | 10/1999 | Ospinal et al. |
| 5,965,805 A | 10/1999 | Watts et al. |
| 5,968,025 A | 10/1999 | Roe et al. |
| 5,968,528 A | 10/1999 | Deckner et al. |
| 6,042,842 A | 3/2000 | Lemann et al. |
| 6,107,537 A | 8/2000 | Elder et al. |
| 6,120,488 A | 9/2000 | Vanruswijck et al. |
| 6,120,783 A | 9/2000 | Roe et al. |
| 6,153,209 A | 11/2000 | Vega et al. |
| 6,166,285 A | 12/2000 | Vanruswijck et al. |
| 6,217,890 B1 | 4/2001 | Paul et al. |
| 4,795,454 C1 | 6/2001 | Dragoo |
| 6,270,486 B1 | 8/2001 | Brown et al. |
| 6,270,487 B1 | 8/2001 | Sheehan et al. |
| 6,290,979 B1 | 9/2001 | Roe et al. |
| 6,315,806 B1 | 11/2001 | Torobin et al. |
| H2013 H | 2/2002 | Boyd et al. |
| 6,372,202 B1 | 4/2002 | Simon |
| 6,403,107 B1 | 6/2002 | Lemann |
| 6,426,444 B2 | 7/2002 | Roe et al. |
| 6,475,197 B1 | 11/2002 | Krzysik et al. |
| 6,476,288 B1 | 11/2002 | Vanrijswijck et al. |
| 6,482,191 B1 | 11/2002 | Roe et al. |
| 6,491,927 B1 | 12/2002 | Arnaud et al. |
| 6,515,029 B1 | 2/2003 | Krzysik et al. |
| 6,570,054 B1 | 5/2003 | Gatto et al. |
| 6,570,055 B2 | 5/2003 | Yang et al. |
| 6,689,932 B2 | 2/2004 | Kruchoski et al. |
| 6,695,992 B2 | 2/2004 | Reneker |
| 6,743,965 B2 | 6/2004 | Yang et al. |
| 6,749,860 B2 | 6/2004 | Tyrrell et al. |
| 6,750,055 B1 | 6/2004 | Connelly et al. |
| 6,756,520 B1 | 6/2004 | Krzysik et al. |
| 6,861,571 B1 | 3/2005 | Roe et al. |
| 7,158,269 B2 | 1/2007 | Morita |
| 7,223,261 B2 | 5/2007 | Müeller et al. |
| 7,273,476 B2 | 9/2007 | Mueller et al. |
| 7,771,735 B2 | 8/2010 | Dvoracek et al. |
| 7,781,641 B2 | 8/2010 | Kasai |
| 8,138,387 B2 | 3/2012 | Vega et al. |
| 2001/0055599 A1 | 12/2001 | Drzewiecki et al. |
| 2002/0016579 A1 | 2/2002 | Stenberg |
| 2002/0120241 A1* | 8/2002 | Tyrrell ............... A61F 13/8405 604/364 |
| 2002/0123731 A1 | 9/2002 | Yang et al. |
| 2003/0082223 A1 | 5/2003 | Healy et al. |
| 2003/0130636 A1 | 7/2003 | Brock et al. |
| 2003/0154904 A1 | 8/2003 | Klofta et al. |
| 2003/0211124 A1 | 11/2003 | Luu et al. |
| 2003/0703233 | 5/2004 | Hoffman et al. |
| 2004/0092900 A1 | 5/2004 | Hoffman et al. |
| 2004/0092901 A1 | 5/2004 | Reece et al. |
| 2004/0092902 A1 | 5/2004 | Hoffman et al. |
| 2004/0162538 A1 | 8/2004 | Mueller et al. |
| 2004/0266300 A1 | 12/2004 | Isele et al. |
| 2005/0008776 A1 | 1/2005 | Chhabra et al. |
| 2005/0058669 A1 | 3/2005 | Krzysik et al. |
| 2005/0095942 A1 | 5/2005 | Mueller et al. |
| 2005/0101927 A1 | 5/2005 | Joseph et al. |
| 2005/0059941 A1 | 7/2005 | Baldwin et al. |
| 2005/0177123 A1 | 8/2005 | Catalan |
| 2005/0203476 A1* | 9/2005 | Stegall ............... A61F 13/55115 604/385.06 |
| 2005/0256476 A1 | 11/2005 | Mirle et al. |
| 2005/0261648 A1 | 11/2005 | Mirle et al. |
| 2005/0276865 A1 | 12/2005 | Buyuktimkin et al. |
| 2006/0014460 A1 | 1/2006 | Isele et al. |
| 2006/0025737 A1 | 2/2006 | Song et al. |
| 2006/0045890 A1 | 3/2006 | Gonzalez et al. |
| 2006/0057922 A1 | 3/2006 | Bond et al. |
| 2006/0058765 A1 | 3/2006 | Mueller et al. |
| 2006/0058766 A1 | 3/2006 | Mueller et al. |
| 2006/0104966 A1 | 5/2006 | Green et al. |
| 2006/0110432 A1 | 5/2006 | Luu et al. |
| 2006/0140924 A1 | 6/2006 | Schroeder et al. |
| 2006/0239955 A1 | 10/2006 | Chandar et al. |
| 2007/0202070 A1 | 8/2007 | Kamachi et al. |
| 2007/0286893 A1 | 12/2007 | Marsh et al. |
| 2008/0200894 A1 | 8/2008 | Gatto et al. |
| 2008/0286224 A1 | 11/2008 | Vega et al. |
| 2008/0286320 A1 | 11/2008 | Vega et al. |
| 2008/0287896 A1 | 11/2008 | Vega et al. |
| 2008/0287900 A1 | 11/2008 | Thornton et al. |
| 2009/0137556 A1 | 5/2009 | Bonnichsen |
| 2011/0070277 A1 | 3/2011 | Vega et al. |

FOREIGN PATENT DOCUMENTS

| | | |
|---|---|---|
| EP | 1444970 A1 | 8/2004 |
| EP | 1173231 B1 | 8/2005 |
| GB | 2263720 A | 8/1993 |
| JP | 60-186965 | 4/1987 |
| JP | 02-084057 | 3/1990 |
| JP | 10-509896 T | 9/1998 |
| JP | 2001-204761 A | 7/2001 |
| JP | 2002-113039 A | 4/2002 |
| JP | 2002-519119 T | 7/2002 |
| JP | 2006-515573 T | 6/2006 |
| JP | 2006-297071 | 11/2006 |
| WO | WO 1992/011830 A2 | 7/1992 |
| WO | WO 1996/016682 | 6/1996 |
| WO | WO 1997/005908 A2 | 2/1997 |
| WO | WO 1997/005909 A2 | 2/1997 |
| WO | WO 1998/029078 A1 | 7/1998 |
| WO | WO 1999/024010 A1 | 5/1999 |
| WO | WO 1999/025288 | 5/1999 |
| WO | WO 1999/045973 A1 | 9/1999 |
| WO | WO 2000/057843 | 10/2000 |
| WO | WO 2000/064500 A1 | 11/2000 |
| WO | WO 2000/064501 A1 | 11/2000 |
| WO | WO 2000/064503 A1 | 11/2000 |
| WO | WO 2000/074740 A1 | 12/2000 |
| WO | WO 2002/034305 A2 | 5/2002 |
| WO | WO 2002/049686 A2 | 6/2002 |
| WO | WO 2002/070026 A1 | 9/2002 |
| WO | WO 2003/028776 | 4/2003 |
| WO | WO 2003/057263 A1 | 7/2003 |
| WO | WO 2004/022115 A1 | 3/2004 |
| WO | WO 2005/035011 A1 | 4/2005 |
| WO | WO 2005/035013 A1 | 4/2005 |
| WO | WO 2005/103354 | 11/2005 |
| WO | WO 2005/112854 A1 | 12/2005 |
| WO | WO 2006/022960 A1 | 3/2006 |
| WO | WO 2007/044569 A2 | 4/2007 |
| WO | WO 2007/105147 | 9/2007 |

* cited by examiner

ABSORBENT ARTICLE COMPRISING A LOTION COMPOSITION FOR REDUCING ADHERENCE OF FECES OR MENSES TO THE SKIN

FIELD OF THE INVENTION

A lotion composition comprised on a body facing surface of an absorbent article such as a diaper, training pants or adult incontinence product, may be used for reducing the adherence of feces or menses to the human skin. The lotion composition comprises at least two compounds wherein one first compound is liquid at 25° C. and at least one second component which is solid at 25° C. An effective amount of the lotion composition is comprised on a body facing surface of an absorbent article which is intended to be worn by a wearer. Absorbent articles herein may have at least a topsheet comprising said lotion composition and absorbent articles may be infant (baby) diapers, including training pants, adult incontinence articles, sanitary napkins, pantyliners and the like. The lotion compositions described herein are believed to reduce the adherence of the menses or feces to the skin, thereby improving the ease of menses or bowl movement (BM) clean up.

BACKGROUND OF THE INVENTION

Disposable absorbent products, such as diapers and sanitary napkins, are known that have a topsheet comprising a lotion, to deliver skin benefits to the skin of the wearer and to sometimes improve the removal of feces or menses from the skin. In recent years the focus has been to deliver lotions to sanitary napkins and diapers that provide extra skin benefits, for example by addition of botanical ingredients or pharmaceutical ingredients to the lotions. Lotions of various types are known to provide various skin benefits, such as prevention or treatment of diaper rash. These lotions can be applied to the topsheet of absorbent articles, and can be transferred to the skin of the wearer during use. The addition of lotion to the topsheet of absorbent articles is also known to provide benefits such as easier BM clean up on the skin.

U.S. Pat. No. 5,968,025 to Roe et al., WO 97/05908, WO 97/05909 and US 2006/140924 describe absorbent articles having lotioned topsheets for reducing adherence of BM to the skin, wherein the lotion compositions are primarily hydrophobic. U.S. Pat. No. 3,489,148 to Duncan et al. teaches a diaper comprising a hydrophobic and oleophobic topsheet wherein a portion of the topsheet is coated with a discontinuous film of oleaginous material. A disadvantage of the diapers disclosed in the Duncan et al. reference and other diapers treated with hydrophobic lotions, is that the hydrophobic and oleophobic topsheets are slow in promoting transfer of urine to the underlying absorbent cores. Since the viscosity of BM and menses is considerably greater than urine, the problems associated with Duncan et al are more profound. Accordingly, there is a continuing need for absorbent articles, such as diapers and catamenial devices having improved fluid handling such that more menses enter into and remain in the device, and less on the skin and hair of the wearer. WO 05/035013, WO 00/64500, WO 00/64501, U.S. Patent Application 2002-120241 and U.S. Pat. No. 6,756,520 describe absorbent articles with hydrophilic lotion compositions for various uses, such as improving moisturization or lubrication, for reducing abrasion of skin, for improving skin health, for enhancing the barrier function of the skin and for prevention and alleviation of skin irritations. WO 02/49686 and WO 02/70026 describe apertured polymeric film webs for absorbent articles which are treated with lotion compositions for improving fluid transfer.

However, there is an unmet need to provide absorbent articles to be worn by a wearer, such as diapers, sanitary napkins and the like, with some means to reduce the adherence of feces or menses to the skin. It is further desirable that removal of any feces or menses is improved after use of the article. Also, desired fluid acquisition and distribution properties should be maintained and wearer comfort should be ensured.

SUMMARY OF THE INVENTION

Embodiments disclosed herein include an absorbent article intended to be worn by a wearer. At least a part of a body faceable surface of that article comprises a lotion composition. The lotion composition comprises at least one first compound which is liquid at 25° C. and at least one second compound which is solid at 25° C. The first compound is a liquid polyethylene glycol and said second compound is a solid fatty compound selected from the group consisting of solid fatty acids, solid fatty alcohol and solid fatty soaps. When the solid fatty compound is a solid fatty acid, then the total amount of liquids is higher than the total amount of solids.

Embodiments disclosed also include an absorbent article, intended to be worn by a wearer, wherein at least a part of a body facing surface of that article comprises a lotion composition. The lotion composition includes at least one first compound which is liquid at 25° C. and at least one second compound which is solid at 25° C. The first compound is a liquid fatty acid ester comprising at least one fatty acid unit and at least one ethylene glycol unit, and the second compound is a solid polyethylene glycol.

DETAILED DESCRIPTION OF THE INVENTION

Herein, "comprise" and "include" mean that other elements and/or other steps which do not affect the end result can be added. Each of these terms encompasses the terms "consisting of" and "consisting essentially of".

Herein, "body facing surface" refers to surfaces of absorbent articles and/or their component materials which face the body of the wearer, while "garment facing surface" refers to the opposite surfaces of the absorbent articles and/or their component materials that face away from the wearer when the absorbent articles are worn. Absorbent articles and components thereof, including the topsheet, backsheet, absorbent core, and any individual layers of their component materials, typically have a body facing surface and a garment facing surface.

Herein, "body" refers to outer layers formed by mammalian epidermal tissues including the skin and hair. The characteristics of the body tend to differ dramatically depending on the position, age, sex, and individual's nature. For example, the skin of babies and young children differs from the skin of adults, and the skin having hair differs from the non-haired skin.

As used herein "absorbent article" refers to devices which are intended to be placed against the skin of a wearer to absorb and contain the various exudates discharged from the body. Examples of absorbent articles include incontinence articles such as diapers; pant-like diapers such as training pants; diaper holders; incontinence briefs. Further examples of absorbent articles are feminine hygiene articles such as tampons, interlabial devices, sanitary napkins and pantiliners. In one embodiment of the present invention, the absorbent articles are incontinence articles such as diapers or pant-like diapers.

As used herein "tampon" refers to any type of absorbent structure which is inserted into the vaginal canal or other body cavities for the absorption of fluid there from. The basic tampon structures are described in U.S. Pat. No. 1,926,900 issued to Haas on Sep. 12, 1933; U.S. Pat. No. 1,946,911 issued to Haas on Jul. 3, 1934; and U.S. Pat. No. 3,322,123 issued to Giswold, et al. on May 30, 1967. As used herein "interlabial absorbent article" refers to an absorbent device that is insertable into the interlabial space of a female wearer for catamenial purposes, incontinence barrier, or both. Suitable interlabial absorbent articles are disclosed in, e.g., U.S. Pat. No. 5,762,644 entitled "Toilet-Disposable Absorbent Interlabial Device" issued to Osborn, et al. on Jun. 9, 1998; PCT Publication No. WO 98/29078 entitled "Thin Comfortable Interlabial Absorbent Structure" published in the name of Osborn, et al. on Jul. 9, 1998; U.S. Pat. No. Des. 404,814 entitled "Interlabial Absorbent Device" issued to Mayer on Jan. 26, 1999; U.S. Pat. No. 6,270,486 entitled "Absorbent Interlabial Device" issued to Brown, et al. on Aug. 7, 2001. As used herein, the terms "panty liner" or "panti-liner" refer to absorbent articles that are less bulky than sanitary napkins which are generally worn by women between their menstrual periods. Suitable absorbent articles are disclosed in, e.g., U.S. Pat. No. 4,738,676 entitled "Pantiliner" issued to Osborn on Apr. 19, 1988.

As used herein "diaper" refers to an incontinence article generally worn by infants, and incontinent persons about the lower torso of the wearer. Suitable diapers are disclosed in, e.g., U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993; and U.S. Pat. No. 5,554,145 issued to Roe et al. on Sep. 10, 1996. As used herein "incontinence article" refers to pads, undergarments, inserts for absorbent articles, capacity boosters for absorbent articles, briefs, bed pads, and the like regardless of whether they are worn by adults or other incontinent persons. Suitable incontinence articles are disclosed in, e.g., U.S. Pat. No. 4,253,461 issued to Strickland, et al. on Mar. 3, 1981; U.S. Pat. Nos. 4,597,760 and 4,597,761 issued to Buell; the above-mentioned U.S. Pat. Nos. 4,704,115; 4,909,802 issued to Ahr, et al.; U.S. Pat. No. 4,964,860 issued to Gipson, et al. on Oct. 23, 1990; and PCT Publication No. WO 92/11830 published by Noel, et al. on Jul. 23, 1992. As used herein "pant-like diaper" refers to an incontinence article having fixed sides and leg openings. Pant-like diapers are placed in position on the wearer by inserting the wearer's legs into the leg openings and sliding the pant-like diaper into position about the wearer's lower torso. Suitable pant-like diapers are disclosed in, e.g., U.S. Pat. No. 5,246,433, issued to Hasse, et al. on Sep. 21, 1993.

As used herein "disposable" is used to describe absorbent articles for single use, which are not intended to be laundered, restored or otherwise reused as an absorbent article after a single use.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

The term "longitudinal", as used herein, refers to a line, axis or direction in the plane of the absorbent article that is generally aligned with (e.g., approximately parallel to) a vertical plane which bisects a standing wearer into left and right body halves when the absorbent article is worn. The terms "transverse" or "lateral" as used herein, are interchangeable, and refer to a line, axis or direction which lies within the plane of the absorbent article that is generally perpendicular to the longitudinal direction.

As used herein, the terms "migrate", "migration", or "migrating" mean a lotion composition moves from one place to another place by way of movement on a material or permeation through an intervening material.

As used herein, the term "transfer" when used in the context of a lotion composition, refers to the lotion composition moving from one area of the absorbent article to the skin of the wearer or to another area on the absorbent article not by way of migration but by way of direct contact with the lotion composition, such as in a blotting effect.

"Applying" to a surface of an absorbent article such as the topsheet, barrier cuff or leg cuff as used herein means that said surface, topsheet, barrier cuff or leg cuff comprises at least a partial layer of the lotion composition on at least part of one of its surface so that at least part of the lotion composition may contact the skin of the wearer in use. To allow contact with the skin, typically the body facing surface of the topsheet, barrier cuff or leg cuff is coated. The lotion composition may also penetrate partly or fully into the surface and may penetrate the respective absorbent article component to which it is applied, e.g. the topsheet, the barrier cuff or the leg cuff.

The unit of all molecular weights given herein is Daltons.

As used herein, the term "particulate material" refers to a component of the lotion composition that is insoluble or non-molecularly dispersible or non-reactive biologically in the lotion composition prior to applying this lotion composition to the absorbent article and that remains in particulate form when applied to the absorbent article. It includes all type of particulate forms such as granules, beads, spheres, micro-spheres, powders, as known in the art.

The terms "reducing the adherence" and "anti-stick" are used synonymously. This means that less residual artificial pasty bowel movement (ABM) remains on the skin when compared to a control without anti-stick lotion composition. Typically, no treatment of the skin results in greater than 30% residual ABM remaining on the skin surface.

A lotion composition beneficial for use may leave less than 30%, including less than about 10%, 8%, 7%, 5%, 4%, 3% or 2% residual ABM on the skin surface as assessed by the method described herein. Skin that is not treated with an anti-stick agent or lotion composition, but is otherwise subjected to the above method, serves as a negative control.

Herein, the terms "feces" and "bowl movement", "BM" are used interchangeably.

Generally, applying a lotion composition as described herein below to one or more surfaces of an absorbent article that are in contact with the skin of the wearer, e.g. the topsheet, reduced feces or menses adherence to the skin can be achieved and improved ease of removal of feces or menses can be obtained after the articles have been used and have been removed from the wearer.

The invention also relates an absorbent article, intended to be worn by a wearer, wherein at least a part of a body facing surface of that article comprises a lotion composition, the lotion composition comprising at least one first compound which is liquid at 25° C. and at least one second compound which is solid at 25° C.

In one embodiment, said first compound is a liquid polyethylene glycol and said second compound is a solid nonionic surfactant with an HLB value of at least 10; or wherein said first compound is a liquid fatty acid ester comprising at least one fatty acid unit and at least one ethylene glycol unit and wherein said second compound is a solid polyethylene glycol.

In one embodiment, said first compound is a liquid polyethylene glycol and said second compound is a solid fatty compounds selected from the group consisting of solid fatty acids and solid fatty soaps.

In one embodiment, when said solid nonionic surfactant is an ethoxylated fatty alcohol, then the HLB value is at least 13.

In one embodiment, when said solid fatty compound is a solid fatty acid, then the total amount of liquids is higher than the total amount of solids.

The invention also relates an absorbent article, intended to be worn by a wearer, wherein at least a part of a body facing surface of that article comprises a lotion composition consisting of a first compound which is liquid at 25° C. and a second compound which is solid at 25° C.

In one embodiment, said first compound is a liquid polyethylene glycol and said second compound is a solid nonionic surfactant with an HLB value of at least 10.

In one embodiment, said first compound is a liquid fatty acid ester comprising at least one fatty acid unit and at least one ethylene glycol unit and wherein said second compound is a solid polyethylene glycol.

In one embodiment, said first compound is a liquid polyethylene glycol and said second compound is a solid fatty compounds selected from the group consisting of solid fatty acids and solid fatty soaps and solid fatty alcohols.

In one embodiment, when said solid nonionic surfactant is an ethoxylated fatty alcohol, then the HLB value is at least 13.

The invention also relates to a process of making an absorbent article, comprising the steps of
(a) providing a lotion composition as described herein;
(b) applying said lotion composition to at least one part of the body facing surface of an absorbent article, wherein said lotion composition is applied in an effective amount for reducing the adherence of feces or menses to the human skin, wherein the absorbent article is an article intended to be worn by a wearer.

Lotion Compositions of the Present Invention

The lotion composition may be flowable (e.g. liquid) at suitable process conditions, e.g. above 50° C. or above 60° C. or above 80° C. or optionally above 100° C., but solid or semi-solid at room temperature (25° C.). The terms semi-solid and non-fluid are used interchangeable herein.

The lotion composition herein may be a lotion composition that may provide additional skin care benefits. The lotion compositions of the present invention are typically non-fluid, i.e. solid, or more often semisolid, at 25° C., i.e. at ambient temperatures. By "semisolid" is meant that the lotion composition has a rheology typical of pseudoplastic or plastic fluids. When no shear is applied, the lotion compositions can have the appearance of a non-fluid, solid but can be made to flow as the shear rate is increased. This may be due to the fact that, while the lotion composition contains solid components, it also includes some liquid components. The lotion compositions of the present invention may be solid or at least semi-solid at room temperature to minimize migration of the lotion composition. The lotion composition may have a final melting point (100% liquid) above potential "stressful" storage conditions that can be 45° C. or greater. Non-fluid means that 1 g of the material, which is placed in the middle of a round glass plate having a diameter of 15 cm, does not run off a glass plate within 1 minute, when the glass plate is tilted at 45°, under conditions of 25° C. and 50% relative humidity.

In one embodiment, the lotion composition is such that 3% to 75% by weight is liquid at room temperature (20° C.). From 25% to 75% or even 30% to 80% can be liquid at body temperature (37° C.). In one embodiment, the total amount of liquid compounds is higher than the total amount of solid compounds, e.g. the amount of liquids is above 50 wt. % or at least 55 wt. % or at least 60 wt. %. When applied to the absorbent article, the lotion compositions of the present invention are transferable to the wearer's skin by normal contact, wearer motion (thus creating friction), and/or body heat.

An effective amount of the lotion composition is comprised on a body facing surface of an absorbent article. An effective amount is an amount which effects a reduction of the adherence of feces or menses to the human skin of a wearer wearing an absorbent article compared to the absorbent article without the lotion composition. Typically, a no treatment control article yield a value of at least 30% residual feces when measured as described herein. Without being bound by theory, it is believed that the lotion composition may reduce the adhesive force between the soils or exudates and the skin surface because the adhesive forces may be smaller than the cohesive forces within the soils or exudates, thereby allowing the soils or exudates to detach from the skin surface upon application of a shear force (e.g. such as that generated by wiping).

Generally, the lotion composition is applied to an absorbent article as described herein in a safe and effective amount, wherein such safe and effective amounts are applied on a least a portion of the topsheet and/or on at least a portion of the barrier cuff and/or at least a portion of the leg cuff. An effective amount according to the present invention may be from about 0.0015 mg/cm$^2$ (0.01 mg/in$^2$) to about 100.5 mg/cm$^2$ (100 mg/in$^2$), from about 0.003 mg/cm$^2$ (0.02 mg/in$^2$) to about 12.4 mg/cm$^2$ (80 mg/in$^2$), or from about 0.02 mg/cm$^2$ (0.015 mg/in$^2$) to about 7.75 mg/cm$^2$ (50 mg/in$^2$), of the lotion composition to the absorbent article. Typically, a safe and effective amount of the lotion compositions of the present invention is applied to an absorbent article such that at least about 0.00015 mg/cm$^2$ (0.001 mg/in$^2$) to about 15.5 mg/cm$^2$ (100 mg/in$^2$), from about 0.0006 mg/cm$^2$ (0.004 mg/in$^2$) to about 11 mg/cm$^2$ (72 mg/in$^2$), or from about 0.005 mg/cm$^2$ (0.03 mg/in$^2$) to about 6.2 mg/cm$^2$ (40 mg/in$^2$), of the lotion composition is transferred to the body during a single use of an absorbent article which is typically about a three hour period. Absorbent articles are generally changed every three to six hours during the day and once for overnight protection, resulting in at least a safe and effective amount of from about 0.00045 mg/cm$^2$ (0.003 mg/in$^2$) to about 124 mg/cm$^2$ (800 mg/in$^2$), from about 0.0018 mg/cm$^2$ (0.012 mg/in$^2$) to about 88 mg/cm$^2$ (576 mg/in$^2$), or from about 0.015 mg/cm$^2$ (0.09 mg/in$^2$) to about 49.6 mg/cm$^2$ (320 mg/in$^2$), of the lotion composition being administered within a one day interval (24 hour period). However, the transfer of the lotion compositions of the present invention onto a wearer's body via an absorbent article described herein can occur for one day, several days, weeks, months, or years at appropriate intervals.

The total amount of the first liquid compounds may be from 3 to 90 wt. % or from 20 to 80 wt. % or from 30 to 70 wt. % based on the total lotion composition and the total amount of the solid second compounds is from 10 to 97 wt. % or from 20 to 80 wt. % or from 30 to 70 wt. % based on the total lotion composition; and the weight ratio of first to second compound is from 1:32 to 9:1 or from 1:9 to 9:1 or from 2:8 to 8:2 or from 3:7 to 7:3.

The lotion composition may be hydrophilic and essentially non-aqueous. Non aqueous means, that the lotion compositions either contain no water or they contain water only in minor amounts such as less than 5 wt. % or even less than 1 wt. %. However, these amounts refer to the lotion composition at the time when the absorbent article is produced, i.e. to the time the lotion composition is applied onto the absorbent article. The lotion compositions of the present invention may be rather hygroscopic, and thus may be able to take up a significant amount of water from the surrounding atmosphere, particularly in an environment with high relative humidity. Thus, when the absorbent article has been stored for a relatively long time, such as several months or even years, it is possible that the amount of water contained in the lotion composition has increased to be more than 5 wt %.

Water solubility of the lotion composition is determined as follows: 100 mg of the lotion composition is applied to a glass slide (2.5 cm×8 cm) of known weight, such that the lotion covers an area of 2.5 cm×5 cm on the glass slide. The slide is then placed in a beaker containing 75 ml of pure water at room temperature. The water with the lotion composition therein is not stirred. After 4 hours the glass slide is removed from the beaker and put in an oven at 60° C., 0% RH to remove the water. After drying it is weighted to determine the residual amount of lotion composition on the slide. The lotion composition of the present invention is water soluble if residual amount of lotion composition on the plate after drying is below 60%, below 20% or below 10%. Such lotion compositions having a relatively good water solubility are considered to be hydrophilic within the meaning of the present invention.

While hydrophobic lotion compositions such as those described in the prior art mentioned above may deliver some level of anti-stick performance, they suffer from several drawbacks including that they tend to leave an undesirable greasy or slippery feel on the skin. Also, they are typically lubricious, reducing interaction of the cleansing implement and the soils or exudates, resulting in smearing and rather poor cleaning. Hydrophilic lotion compositions overcome many of these drawbacks. Hydrophilic lotion compositions typically do not leave a greasy feeling on the skin, and they are typically not as lubricous as non-water soluble, hydrophobic lotion compositions which may result in better cleaning and less smearing.

The lotion composition comprises at least one first compound which is liquid at 25° C. and at least one second compound which is solid at 25° C., wherein said first compound is a liquid polyethylene glycol and said second compound is a solid nonionic surfactant with an HLB value of at least 10; or wherein said first compound is a liquid fatty acid ester comprising at least one fatty acid unit and at least one ethylene glycol unit and wherein said second compound is a solid polyethylene glycol; or wherein said first compound is a liquid polyethylene glycol and said second compound is a solid fatty compounds selected from the group consisting of solid fatty acids and solid fatty soaps and solid fatty alcohols;

wherein when said solid nonionic surfactant is an ethoxylated fatty alcohol, then the HLB value is at least 13.

When said solid fatty compound is a solid fatty acid, then the total amount of liquids may be higher than the total amount of solids.

Liquid Polyhydric Alcoholic Solvents

Liquid polyhydric alcoholic solvents, when used herein, are organic compounds having at least 2 carbon atoms and at least two alcoholic hydroxy groups and which are liquid at 25° C., excluding for the purpose of the invention polyethylene glycols, polypropylene glycols and derivatives, as described herein below, as separate groups. Examples are glycerol, ethylene glycol, diethylene glycol, propylene glycol, butylene glycol, dipropylene glycol, methyl propanediol and derivatives thereof, including for example mono- or di-end capped diethylene glycols, mono- or di-end capped dipropylene glycols, mono- or di-end capped ethylene glycols and mono- or di-end capped propylene glycols, having end-capped units as described above.

Liquid compounds herein may include: ethoxylated fatty acids, such as PEG-8 laurate, available for example as Lipopeg 4-L from Lipo Chemicals; ethoxylated fatty ester (oil), such as a PEG-25 castor oil, for example available as hetoxide C-25 from Global-Seven Inc.; Glycerol esters, such as for example a PEG-10 polyglyceryl-2 laurate, available for example as Hostacerin DGL from Clariant Corp.; Lecithin, such as available as Alcolec BS from American Lecithin Co.; polymeric surfactants such as a C8-C10 alkyl polysaccharide ether, available for example as Glucopan 225 DK from Cognis Corp.); Sorbitan derivatives such as POE (20) sorbitan monopalmitate available for example from Croda Inc.; sucrose and glucose esters and derivatives, such as alkyl polyglucoside, available for example as Simulsol AS48 from Seppic Inc.

Liquid Polyethylene Glycols and Derivatives and Liquid Polypropylene Glycol and Derivatives.

Liquid polyethylene glycols and derivatives are liquid at 25° C. The polyethylene glycols (PEG's) are made from at least 3 units of ethylene glycol and have the general formula $HO-(CH2-O-CH2-O)_x-H$ with x being a number of from 3 to 15 or from 8 to 12. The molecular weight (weight average) is from 100 to less than 720, or from 100 or 350 to 700. Typical liquid polyethylene glycols are known as PEG-4, PEG-6, PEG-7, PEG-8, PEG-9, PEG-10, PEG-12 and PEG-14. Suitable trade products are for example Polyglykol 400 of Clariant with an average molecular weight of 380 to 410 or Polyglykol 600 with an average molecular weight of 570 to 630.

Liquid PEG and PPG derivatives may include esters and ethers of PEG and PPG. Liquid derivates of PEG and PPG include in particular PEG's and PPG's (for example as described above) having however one or more (mono or di end capped, respectively) end cap groups, derived from an organic compound capable of reacting with a hydroxyl group. End cap groups may include methyl, ethyl, propyl, isopropyl, butyl, isobutyl, tert-butyl and benzyl, for example mono- or di-methyl or -ethyl end capped PEG or PPG. In some embodiment, methyl may be an end-capping unit. Further polypropylenes and end capping units useful in this invention are described in co-pending application U.S. 60/901,793, filed 16 Feb. 2007.

A liquid mono-end capped PEG may include for example a polyethylene glycol monomethyl ether, such as available as Polyglykol M400 from Clariant Corporation. A liquid PEG may include also a Polyethylene glycol dimethyl ether with a MW of 500 (available from Sigma Aldrich).

Also useful herein are liquid ethylene oxide—propylene oxide copolymers and polyethylene—polypropylene block copolymers (EO-PO block copolymers), such as Genapol PF10—an EO-PO block copolymer from Clariant Corp.)

Liquid Alkylene (e.g. Ethylene) Glycol Fatty Acid Esters

Suitable liquid alkylene or ethylene glycol fatty acid esters are for example the esters of one or more alkylene glycol units, including ethylene glycol units, and one or two fatty acids. These compounds may have the general formula $R^1$—(OCH2CH2)$_m$O—$R^2$ where $R^1$ and $R^2$ are hydrogen or fatty acid residues with e.g. from 6 to 30 or from 8 to 22 carbon atoms and can be the same or different with the proviso that not both are hydrogen; and m is a number of at least 1. R1 and R2 may be different and m may be 1, 2, or 3. Typical ethylene glycol esters are known for example as diethylene glycol diethylhexanoate/diisononanoate, diethylene glycol diisononanoate, diethylene glycol dilaurate, diethylene glycol dioctanoate/diisononanoate and diethylene glycol distearate. Suitable trade product mixtures containing ethylene glycol esters are for example DERMOL MO or DERMOL 489. Wax esters may be used which are liquid at room temperature (25° C.). They may be derived from natural sources such as jojoba oil, comprising docosenyl eicosenoate, eicosenyl eicosenoate and eicosenyl docosenoate.

Solid Polyethylene Glycol and Polypropylene Glycols and Derivatives Thereof

Solid polyethylene glycols, polypropylene glycols and derivatives thereof are solid (or semi-solid—as defined above) at 25° C., as defined herein. The solid polyethylene glycols are typically made from at least 16 units of ethylene glycol and have the general formula HO—(CH2-O—CH2-O)$_y$—H with y being a number of at least 16, e.g. from 20 to 220 or from 40 to 150. The molecular weight (weight average) is above 720, e.g. from 720 to 100000, or from 950 or 1500 or 2000 or 2700 to 30000. Typical solid polyethylene glycols are known as PEG-20, PEG-32, PEG-40, PEG-45, PEG-55, PEG-60, PEG-75, PEG-90 and PEG-100. Suitable trade products are for example Polyglykol 3000 of Clariant with an average molecular weight of 2700 to 3000 or Polyglykol 4000 with an average molecular weight of 3700 to 4500.

Solid PEG and PPG derivatives may include esters and ether derivates of PEG's and PPG's. Solid derivatives include in particular PEG's and PPG's (for example as described above) having one or more end cap groups (mono or di end capped, respectively), such as those described above.

For example, a solid mono-end capped PEG such as Polyglykol M4000 (polyethylene glycol monomethyl, from Clariant Corporation) may be used and/or a solid di-end-capped PEG such as Polyethylene glycol dimethyl ether MW2000 (from Sigma Aldrich) may be used.

Also useful herein may be solid EO-PO copolymers and EO-PO block copolymers, such as for example Genapol PF80, an EO-PO block copolymer from Clariant Corp.

Solid Nonionic Surfactants

Suitable solid nonionic surfactants with an HLB value of at least 10 include solid PEG derived nonionic surfactants, solid polyalkylene glycol fatty alcohol ethers, such as solid polyethylene glycol fatty alcohol ethers or for example solid polyethoxylated fatty alcohols. The fatty alcohols unit may have from 8 to 30 carbon atoms, or from 12 to 22 carbon atoms. The average degree of alkoxylation, e.g. ethoxylation, may be from 2 to 200, at least 10, at least 20 or at least 30. These surfactants may be nonionic surfactants with HLB values of at least 10, or at least 12 or at least 13, up to for example 17. Polyethylene glycol fatty alcohol ethers have the general formula R(OCH2CH2)$_n$OH, where R represents an alkyl group or a blend of alkyl groups with for example 8 to 30 or 12 to 22 carbon atoms and n is the degree of ethoxylation, e.g. 2 to 200. Suitable PEG derived surfactants include PEG-12 stearate, PEG-100 stearate, for example available as Tego Acid S100 P from Evonik/Degussa.

Suitable trade products include also for example BRIJ 76, BRIJ 78 and BRIJ 700 (Steareth 100, available from Croda Inc.).

Other surfactants may include Ceteraeth-10, Ceteareth-20, Polysorbate-65. Also used may be Laureth 23.

Suitable fatty alcohol fatty acid esters are esters of a C10- to C30 fatty alcohol with a C10- to C30-fatty acid. They have the general formula $R^3$—CO—O—$R^4$ where $R^3$—CO is a C10- to C30 fatty acid residue and O—$R^4$ is a C10- to C30 fatty alcohol residue. They may be saturated or unsaturated.

Other suitable nonionic surfactant are e.g. ethoxylated alcohols, ethoxylated fatty acids, ethoxylated fatty esters and oils, glycerol esters; sucrose and glucose esters and their derivatives, glucosides, sorbitan derivatives, such as sorbitan monoplamitate.

Other compounds may include PEG oils, like PEG40 hydrogenated caster oil, PEG-20 sorbitan monooleate, PEG-200 castor oil, available for example as Hetoxide C-200 from Global-Seven Inc.; glycerol esters such as a decaglycerol mono/dioleate, available for example as Caprol PGE860 from Abitec Corp.; lecithin derivatives, such as soy phosphatides, such as available as Alcolec Powder from American Lecithin Co.; sorbitan derivatives, such as Polysorbate 65, such as available as Liposorb TS-20 from Lipo Chemicals; sucrose and glucose esters and derivatives such as succinoglycan, available for example as Rheozan from Rhodia, Inc.

Solid Fatty Compounds:

The solid fatty compounds are selected from the group consisting of: fatty acids, solid fatty soaps and solid fatty alcohols. The solid fatty compounds are solid at (or at least semi-solid according to the method described herein, at 25° C.). The fatty compounds may have from 10 to 30 or from 12 to 22 carbon atoms. The fatty compounds can be saturated or unsaturated and they can be linear or branched. They may be saturated, linear fatty compounds. Examples of solid fatty acids are decanoic acid, lauric acid, myristic acid, palmitic acid, stearic acid, arachidic acid or behenic acid. Solid fatty alcohols may be linear, unsaturated 1-alkanols with at least 12 carbon atoms. Examples of solid fatty alcohols are lauryl alcohol, myristyl alcohol, cetyl alcohol, stearyl alcohol, arachidyl alcohol or behenyl alcohol.

The solid fatty soaps are metallic soaps which are metal salts of fatty acids. The fatty acid components of the fatty soaps are the same as mentioned above. Suitable metal cations are sodium, potassium, lithium, aluminium, magnesium, calcium, mangan, iron, zirconium, cerium, zinc, cobalt or vanadium. Metallic soaps may be used with low water solubility such as the calcium or magnesium salts, e.g. calcium stearate.

Exemplary Compositions:

It may be that the first liquid component comprises one or more compounds selected from the group consisting of: methoxyisopropanol, propyl ether, dipropylene glycol butyl ether, methyl propanediol, propylene carbonate, ethylene glycols, diethylene glycols, propylene glycols, dipropylene glycols, glycerin, sorbitol, hydrogenated starch hydrolysate, silicone glycols, or any of the above mentioned or exemplified polyethylne glycol or derivatives, polypropylene glycol or derivatives, polyethylene glycol derived surfactants, polypropylene derived surfactants, ethylene glycol or derivatives, propylene glycol or derivatives, diethylene glycol or derivatives and dipropylene glycol or derivatives, as described herein.

The second, solid component may comprise for example one or more solid compounds (as defined above) of the group including: solid polyethylene glycol or derivatives thereof; solid polypropylene glycol or derivatives thereof; solid nonionic surfactants with HLB value of at least 10; solid fatty compounds selected from the group consisting of solid fatty acids, solid fatty soaps and solid fatty alcohols; solid PEG derived surfactants; solid PPG derived surfactants; ethoxylated natural fats or propoxylated natural fats, such as PEG-150 jojoba.

Exemplary lotion compositions may be such that:

said first liquid component may comprise a liquid polyethylene glycol and said second component may comprise a solid nonionic surfactant with an HLB value of at least 10, provided that when said solid nonionic surfactant is an alkoxylated (e.g. ethoxylated) fatty alcohol, then the HLB value is at least 13; or said first component may comprise a liquid fatty acid ester comprising at least one fatty acid unit and at least one ethylene glycol unit and said second component may comprise a solid polyethylene glycol; or said first component may comprise a liquid polyethylene glycol and said second compound is a solid fatty compounds selected from the group consisting of solid fatty acids and solid fatty soaps and solid fatty alcohols.

When said solid fatty compound comprises a solid fatty acid, then the total amount of liquids may be higher than the total amount of solids.

In one embodiment the liquid component is a polyethylene glycol having a molecular weight (weight average) of 100 to less than 720, or from 350 to 700. It may be that the lotion composition comprises from 20% to 80% by weight, or 30% to 70% by weight, or 40% to 60% by weight of this liquid polyethylene glycol. For example 50% by weight of polyethylene glycol with a MW of 400, also referred to as Polyglycol 400.

In one embodiment the solid component is a polyethylene glycol or derivative, where appropriate, having a molecular weight (weight average) of above 720, e.g. from 720 to 100000, or from 950 to 30000, or from 3000 to 20000 or to 10000. It may be that the lotion composition comprises from 20% to 80% by weight, or 30% to 70% by weight, or 40% to 60% by weight of this liquid polyethylene glycol, for example 50% by weight of Polyglycol 4000.

In one embodiment the solid component is a solid non-ionic surfactant, or a solid polyethylene glycol fatty alcohol ethers having the general formula $R(OCH2CH2)_nOH$, where R represents an alkyl group or a blend of alkyl groups, with for example 8 to 30 or 12 to 22 carbon atoms, and n is the degree of ethoxylation, e.g. 2 to 200. It may be that the lotion composition comprises from 20% to 80% by weight, or 30% to 70% by weight, or 40% to 60% by weight of this liquid polyethylene glycol, for example 50% by weight of Steareth-100.

Particulate Material

In one embodiment, the lotion composition additionally comprises at least one particulate material for further reducing the adherence of feces or menses to the skin. The particulate material is particulate during application onto the absorbent article. The particulate material is also such that it remains particulate when in contact with the skin and/or when in contact with urine, menses or feces. Hence, the particulate material is water-insoluble and it has a melting temperature above the processing temperature of the lotion composition, as described above.

The particulate material may have any mean particle size between 1 nanometer to 2 mm, between 1 nanometer to 500 micrometers, between 0.1 micrometer to 2 mm, between 50 nanometers to 1 micrometer, or any range or individual value within any of the ranges set forth herein. The minimum mean particle size may be at least 0.1 micrometer or at least 1 micrometer, or at least 10 micrometers, or at least 20 micrometers, or up to about 500 micrometers or in some embodiments up to about 100 micrometers, and further in other embodiments up to about 30 micrometers. In one embodiment, it may be that the lotion composition to be applied and/or the applied coating comprises particles whereof less than 25% of the particles have an equivalent diameter of greater than 100 microns. In another embodiment, it may be that the lotion composition to be applied and/or the applied coating comprises particles whereof less than 25% of the particles have an equivalent diameter of less than 5 microns. In yet another embodiment, it may be that the lotion composition to be applied and/or the applied coating comprises particles whereof less than 25% of the particles have an equivalent diameter of less than 100 microns.

The particle material may be present in the lotion composition at a level from 0.05% to 25% (by weight of the lotion composition), from 0.05% to 15%, from 0.05% to 5%, or from 0.1% to 25%, or from 0.25% to 20%, or from 0.5% to 10% or even up to 5% by weight.

Suitably, the particles may have a density between about 0.5 gram/cm$^3$ and about 2.5 gram/cm$^3$. The density may be between about 0.5 gram/cm$^3$ and about 2.0 gram/cm$^3$, or between 0.8 gram/cm$^3$ and about 1.5 gram/cm$^3$. In one embodiment, the density may be less than about 1 gram/cm$^3$ so as to minimize particle settling and the density is greater than about 0.8 gram/cm$^3$ so as to minimize particle floatation.

In one embodiment, the lotion composition may comprise inorganic particles, including alumina silicates, silicates, silicas, mica and/or talc. Clays may also be used. However, in the present invention it may be that the particulate material is an organic material. The particles may be a non-active and/or non-reactive material. The particles may be porous, or non-porous. The particles may have any shape, but they may have a smooth surface, and they may be spherical or plate-like particles. The particles may comprise a coating agent on their surface or part thereof, for example a surfactant to change its properties, e.g. hydrophilicity. The particles, in particular when they are oleofinic, may include a melt-additive, which is added during the manufacturing of the particles.

Suitable materials include but are not limited to: polystyrene particles, polypropylene and/or polyethylene (co)polymer particles, polytetrafluoroethylene particles, polymethylsilses-quioxane particles, nylon particles. Suitable commercially available particulate materials include but are not limited to: polyethylene particles, available from Honeywell International of Morristown, N.J. under the trade name ACUMIST; polymethyl methacrylate particles (microspheres), available from KOBO of South Plainfield, N.J. as BPA; lactone cross polymer particles (microspheres), available from KOBO as BPD; nylon 12 particles (microspheres), available from KOBO as NYLON SP; polymethylsilsesquioxane particles (microspheres), available from KOBO as TOSPEARL; cellulose particles (microspheres), available from KOBO as CELLO-BEADS; polytetrafluoroethylene powders, available from Micro Powders, Inc. of Tarrytown, N.Y. as MICROSLIP; blends of natural wax and micronized polymers as are available from Micro Powders as MICROCARE and particles of a copolymer of vinylidene chloride, acrylonitrile and methylmethacrylate available as EXPANCEL from Expancel, Inc. of Duluth, Ga. Micronized waxes, such as are available from Micro Powders as MICROEASE may also be incorporated. Polyolefin particles (powders) may be used as are available from Equistar Chemical Corp. Houston, Tex. as MICROTHENE. MICROTHENE FN510-00 from Equistar may be used.

Optional Ingredients

In order to better enhance the benefits to the wearer, additional ingredients can be included in the lotion compositions of the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors); film formers (to hold active ingredients on the skin by producing a continuous film on skin upon drying); fragrances (consumer appeal); humectants (increase the water content of the top layers of the skin); natural moisturizing agents (NMF) and other skin moisturizing ingredients known in the art; opacifiers (reduce the clarity or transparent appearance of the product); skin conditioning agents; other solvents (liquids employed to dissolve components found useful in the cosmetics or drugs); and other surfactants (e.g. as cleansing agents, emulsifying agents, solubilizing agents, and suspending agents). Suitable anionic surfactants are e.g. phosphate esters, carboxylic acids/fatty acids, lignin and lignin derivatives, polyacrylic acid copolymers. Suitable catione surfactants are e.g. ethoxylated amines, quaternary surfactants, phospholipids, amine oxides. Suitable amphoteric surfactants are e.g. betaine derivatives, imidazolines and imidazoline derivatives, lecithin.

Suitable anti-foaming agents for use in the present lotion composition are e.g. 2-ethylhexanol, polydimethyl siloxane, glyceryl monooleate, glycols, ethylene oxide/propylene oxide block polymers.

Suitable antimicrobial agents for use in the present lotion composition are e.g. alkyl dimethyl benzyl ammonium chloride, sulfonamides, essential oils (tea tree oil), silver, ethanol, triclosan, clay.

Suitable antifungal agents for use in the present lotion composition are e.g. benzoic acid, parabens, polyaminopropyl biguanide, tea tree oil, chlorphenesin.

Suitable antiseptic agents for use in the present lotion composition are e.g. benzalkonium chloride, ethanol, chlorhexidine, iodopropyl butyl carbamate.

Suitable antioxidants for use in the present lotion composition are e.g. tocopherol (Vitamin E) and derivatives thereof, butylated hydroxytoluene, propyl gallate, nonylphenol, ascorbic acid (Vitamin C) and derivatives thereof.

Suitable cosmetic astringents for use in the present lotion composition are e.g. witch hazel, calamine, SD alcohol, zinc oxide, oatmeal, cucumber.

Suitable drug astringents for use in the present lotion composition are e.g. ammonium alum, zinc chloride.

Suitable biological additives for use in the present lotion composition are e.g. allantoin, chitosan, collagen, glycoproteins, phospholipids.

Suitable botanical additives for use in the present lotion composition are e.g. *Echinacea, yucca*, willow herb, green tea, black tea, Chinese tea, chamomile, aloe and lavender Suitable colorants for use in the present lotion composition are e.g. beta carotene, FD&C certified colors, titanium dioxide, FD&C dyes, mica.

Suitable deodorants for use in the present lotion composition are e.g. baking soda, cetylpyridium chloride, zeolite, triclosan, zinc ricinoleate.

Suitable emollients for use in the present lotion composition are e.g. petrolatum, cocoa butter, triglycerides, cyclomethicone, jojoba wax.

Suitable external analgesics for use in the present lotion composition are e.g. benzyl alcohol, camphor, menthol, methyl nicotinate, and resorcinol.

Suitable film formers for use in the present lotion composition are e.g. acrylates copolymer, cellulose gum, polyethylene, PVP, and polyquaterniums.

Suitable fragrances for use in the present lotion composition are e.g. benzyl alcohol, chamomile oil, lavender oil, menthyl lactate, farnesol.

Suitable humectants for use in the present lotion composition are e.g. glycerin, honey, urea, sucrose, PEG-4.

Suitable moisturizing agents for use in the present lotion composition are e.g. aloe extract, glycerin, ceteth-24, lanolin, PEG-40 stearate, sodium lactate, water.

Suitable opacifiers for use in the present lotion composition are e.g. cetyl alcohol, silica, kaolin, zinc carbonate, talc.

Suitable skin protectants for use in the present lotion composition are e.g. calamine, dimethicone, mineral oil, kaolin, zinc oxide.

Suitable solvents for use in the present lotion composition are e.g. benzyl alcohol, isoparaffins, glycol, PEG-4, propylene glycol, mineral oil.

Suitable cleansing agents for use in the present lotion composition are e.g. cocoamidopropyl betaine, decylpolyglucoside, C20-40 pareth-40, steareth-50, PEG-100 stearate.

Suitable emulsifiers for use in the present lotion composition are e.g. ceteth-10, glyceryl palmitate, lecithin, PEG-10 stearate, sucrose laurate.

Suitable solubilizing agents for use in the present lotion composition are e.g. ceteareth-40, PEG-40 castor oil, poloxamers, PEG-40 stearate, polysorbates.

Suitable suspending agents for use in the present lotion composition are e.g. benzalkonium chloride, polysorbate 85, sodium lignosulfonate, acrylates copolymer, bentonite, PEI, PVP, silica.

Suitable binders for use in the present lotion composition are e.g. alginic acid, cellulose gum, gelatin, starch, synthetic or natural wax.

Suitable absorbents for use in the present lotion composition are e.g. cellulose, dextrin, starch, kaolin, silica, talc.

Suitable buffering agents for use in the present lotion composition are e.g. calcium carbonate, sodium citrate, urea, disodium phosphate, and glycine.

Suitable fats or oils for use in the present lotion composition are e.g. avocado oil, caprilic triglyceride, capric triglyceride, lauric triglyceride, carrot oil, coconut oil, walnut oil, hydrogenated fish oil.

Optional ingredients according to the present invention may include botanical additives, antimicrobial agents, antiseptic agents and antifungal agents.

Absorbent Articles a) Incontinence Articles

In the following, a diaper is described as one embodiment of an incontinence article. However, as the skilled person is aware of, most of the components and materials described herein below are also applicable to other incontinence articles such as pant-like diapers.

The diaper has a longitudinal axis and a transverse axis. The diaper has further an inner, body facing surface and an outer, garment facing surface opposed to the inner surface.

One end portion of the diaper is configured as a front waist region of the diaper. The opposite end portion is configured as a back waist region of the diaper. An intermediate portion of the diaper is configured as a crotch region, which extends longitudinally between the front and back waist regions. The crotch region is that portion of the diaper which, when the diaper is worn, is generally positioned between the wearer's legs.

The chassis of the diaper comprises the main body of the diaper. The chassis comprises a liquid pervious topsheet and a backsheet. The chassis further includes an absorbent core encased between the topsheet and the backsheet. The chassis has a periphery which is defined by the transverse outer edges of the chassis with longitudinal edges and end edges. The diapers, pant-like diapers or adult incontinence products herein typically have also leg cuffs and/or barrier cuffs.

The backsheet may typically be a liquid impervious backsheet, as known in the art. In one embodiment, the liquid impervious backsheet comprises a thin plastic film such as a thermoplastic film having a thickness of about 0.01 mm to about 0.05 mm. Suitable backsheet materials comprise typically breathable material, which permit vapors to escape from the absorbent article while still preventing exudates from passing through the backsheet. Suitable backsheet films include those manufactured by Tredegar Industries Inc. of Terre Haute, Ind. and sold under the trade names X15306, X10962 and X10964. The backsheet, or any portion thereof, may be elastically extendable in one or more directions.

The topsheet may be compliant, soft feeling, and non-irritating to the wearer's skin. Further, the topsheet is liquid pervious permitting liquids (e.g., urine) to readily penetrate through its thickness. A suitable topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be made of natural fibers (e.g., wood or cotton fibers), synthetic fibers (e.g., polymeric fibers such as polyester, polypropylene, or polyethylene fibers) or from a combination of natural and synthetic fibers. The topsheet may be made of a hydrophobic material to isolate the wearer's skin from liquids which have passed through the topsheet and are contained in the absorbent core (i.e., to prevent rewet). If the topsheet is made of a hydrophobic material, at least the body facing surface of the topsheet or a part thereof may be treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. In one embodiment, the topsheet is a nonwoven web that can provide reduced tendency for surface wetness and consequently facilitate maintaining urine absorbed by the core away from the user's skin, after wetting.

The absorbent article herein may have one or more pairs of (elasticated) leg cuffs, including so-called side panels, and/or (elasticated) barrier cuffs that provide improved containment of liquids and other body exudates, and these cuffs may in one embodiment comprise the coating lotion composition described herein. Suitable cuffs are described in for example U.S. Pat. Nos. 3,860,003; 4,808,178 and 4,909; U.S. Pat. Nos. 4,695,278 and 4,795,454. The cuffs may also be made of nonwoven materials as described above and they may be hydrophobic.

Suitable materials for the topsheet and/or the leg cuffs and/or the barrier cuffs include webs comprising spunbond layers (S) and meltblown layer(s) (M), whereby the surfaces of the web are formed by spunbond layer(s). In one embodiment, the webs may have a relatively high basis weight, for example more than 25 g/m$^2$ (gsm). Suitable webs include, for example, 34 gsm SMMS (with 12 gsm for each meltblown and 5 gsm for each spunbond layer); 34 gsm SMMS (with 10 gsm for each meltblown and 7 gsm for each spunbond layer); 30 gsm SMMS (with 10 gsm for each meltblown and 5 gsm for each spunbond layer); 30 gsm SMMS (with 8 gsm for each meltblown and 7 gsm for each spunbond layer); 34 gsm SMS (with 20 gsm for the meltblown and 7 gsm for each spunbond layer), or, for example, laminate webs comprising two webs of 17 gsm SMMS laminated to each other.

The backsheet may be directly or indirectly attached to or joined with the topsheet herein and/or the barrier and/or leg cuffs herein.

The absorbent core generally is disposed between the topsheet and the backsheet. The absorbent core may comprise any absorbent material that is generally compressible, conformable, non-irritating to the wearer's skin, and capable of absorbing and retaining liquids such as urine and other certain body exudates.

The absorbent core may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied, e.g. the absorbent core may have varying caliper zones, a hydrophilic gradient, a superabsorbent gradient, or lower average density and lower average basis weight acquisition zones; or may comprise one or more layers or structures. The total absorbent capacity of the absorbent core should, however, be compatible with the design loading and the intended use of the diaper. Further, the size and absorbent capacity of the absorbent core may be varied to accommodate wearers ranging from infants through adults.

The topsheet of the absorbent article of the present invention can also be apertured, i.e. the topsheet has a plurality of apertures having an aperture size of at least about 0.2 mm². The topsheet may have an open area of at least about 10%, the open area being the sum of all apertures.

The topsheet herein may also be a topsheet that has one or more openings that are large enough to let feces (or menses) pass to a void space underneath said secondary topsheet, also referred to as anal cuff or vaginal cuff. For example, U.S. Patent Application No. 2006/0058766 A filed on Sep. 13, 2005 discloses an absorbent article wherein the topsheet is provided with at least one opening adapted to receive fecal material, the topsheet and the opening thereof each having a front region and a back region. A void space between the absorbent core and the topsheet is provided and the absorbent article further comprises a genital coversheet, which in use covers the genitals, and which is positioned in, under or above said front region of the opening. Further suitable absorbent articles are disclosed e.g. in U.S. Pat. No. 6,482,191; U.S. Patent Application No. 2004/0092902 A; U.S. Patent Application No. 2004/0092900 A; U.S. Patent Application No. 2004/0162538 A; and U.S. Patent Application No. 2006/0058765 A.

Further, the incontinence articles may comprise a front and back waist band and/or a fastening system, typically joined to the waistband, as known in the art. Fastening systems may comprise fastening tabs and landing zones, wherein the fastening tabs are attached or joined to the back region of the diaper and the landing zones are part of the front region of the diaper.

b) Feminine Hygiene Articles

In one embodiment, the lotion compositions of the present invention may be transferred to the body from application of the lotion compositions onto a feminine hygiene article. These products may comprise a topsheet, a backsheet, and an absorbent core positioned between the topsheet and backsheet; each component having a body facing surface and a garment facing surface.

The absorbent article may comprise any known or otherwise effective topsheet, such as one which is compliant, soft feeling, and non-irritating to the wearer's body. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, also provides for the transfer or migration of the lotion composition onto an external or internal portion of a wearer's body. A suitable topsheet can be made of various materials such as woven and nonwoven materials; apertured film materials including apertured formed thermoplastic films, apertured plastic films, and fiber-entangled apertured films; hydroformed thermoplastic films; porous foams; reticulated foams; reticulated thermoplastic films; thermoplastic scrims; or combinations thereof, as is well known in the art of making feminine hygiene articles such as sanitary napkins, pantiliners, and the like.

When the topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The feminine hygiene article of the present invention also comprises a backsheet. The backsheet can be any known or otherwise effective backsheet material, provided that the backsheet prevents external leakage of exudates absorbed and contained in the feminine hygiene article. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof, as is well known in the art of making feminine hygiene articles such as sanitary napkins, pantiliners, and the like.

The feminine hygiene article also comprises an absorbent core. The absorbent core is typically positioned between the topsheet and the backsheet. The size and shape of the absorbent core can be altered to meet absorbent capacity requirements, and to provide comfort to the wearer/user. The absorbent core suitable for use in the present invention can be any liquid-absorbent material known in the art for use in absorbent articles, provided that the liquid-absorbent material can be configured or constructed to meet absorbent capacity requirements. Nonlimiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof, as is well known in the art of making feminine hygiene articles such as sanitary napkins, pantiliners, and the like.

The sanitary napkins or panty-liners herein may comprise as cuffs so-called wings, for example attachment to underwear of the wearer. The sanitary napkins and/or panty-liners herein may comprise a fastening means comprised by the backsheet and/or by the wings (cuffs). Adhesive attachment means may be used that are present on or attached to at least the backsheet.

c) Combination of Absorbent Article Comprising the Lotion Composition of the Present Invention and a Wipe The absorbent articles comprising the lotion composition of the present invention can be packaged together with one or more wipes for use in the cleaning and removal of soils or exudates. It is also possible to have one absorbent article together with one or more wipes as one individual package, which is especially convenient for users en-route, where it might be desirable to carry only one absorbent article and one wipe or only one absorbent article and a few wipes. Alternatively, a number of absorbent articles comprising the lotion composition of the present invention are packaged together with a number of wipes. In the latter case, the number of absorbent articles can be the same as the number of wipes or the number of wipes is higher than the number of absorbent articles.

For combinations of one or more absorbent articles with one or more wipes, it may be that the absorbent article is an incontinence article.

The wipes can be a dry wipe or a wet wipe. In one embodiment, the wipes are lotioned wipes, i.e. the wipes comprise a lotion which provides an anti-stick effect. However, typically the anti-stick lotion applied on the wipe will be different from the anti-stick lotion applied on the absorbent article.

Lotioned wipes may comprise a substrate and a lotion in contact with the substrate, wherein the lotion comprises an anti-stick agent and a performance enhancing agent, such as is disclosed e.g. in U.S. application Ser. No. 60/855,427 filed on Oct. 31, 2006 and assigned to R. M Marsh et al. The performance enhancing agent may be present at a concentration of equal to or less than about 3% w/w of the lotion. The anti-stick agent may be water soluble.

The anti-stick agent may be selected from the group consisting of non-polymeric anti-stick agents, polymeric anti-stick agents, alkoxylated polyols, and combinations thereof. The performance enhancing agent may be selected from the group consisting of film formers, deposition aids, rheology modifiers and combinations thereof.

The lotion may further comprise an emollient and a surfactant.

"Substrate" is the general term to describe a piece of material, generally non-woven material, used in cleansing body parts. In particular, many currently available substrates may be intended for the cleansing of the perianal area after defecation. Other substrates may be available for the cleansing of the face or other body parts.

The substrate may be a nonwoven material. "Nonwoven" refers herein to a fibrous structure made from an assembly of continuous fibers, coextruded fibers, non-continuous fibers and combinations thereof, without weaving or knitting, by processes such as spunbonding, carding, meltblowing, airlaying, wetlaying, coform, or other such processes known in the art for such purposes. The nonwoven structure may comprise one or more layers of such fibrous assemblies, wherein each layer may include continuous fibers, coextruded fibers, noncontinuous fibers and combinations thereof.

The fibers of the substrate may be any natural, cellulosic, and/or wholly synthetic material. Examples of natural fibers may include cellulosic natural fibers, such as fibers from hardwood sources, softwood sources, or other non-wood plants. The natural fibers may comprise cellulose, starch and combinations thereof.

The substrate may have a basis weight between about 15, 30, 40 or 45 grams/m$^2$ and about 65, 75, 85, 95 or 100 grams/m$^2$. A suitable substrate may be a carded nonwoven comprising a 40/60 blend of viscose fibers and polypropylene fibers having a basis weight of 58 grams/m$^2$ as available from Suominen of Tampere, Finland as FIBRELLA™ 3160. FIBRELLA™ 3160 is a 58 grams/m$^2$ nonwoven web comprising 60% w/w 1.5 denier polypropylene fibers and 40% w/w 1.5 denier viscose fibers. Another suitable material may be FIBRELLA™ 3100 which is a 62 grams/m$^2$ nonwoven web comprising 50% w/w 1.5 denier polypropylene fibers and 50% w/w 1.5 denier viscose fibers. In both of these commercially available fibrous webs, the average fiber length is about 38 mm. Another suitable material for use as a substrate may be SAWATEX™ 2642 as available from Sandler AG of Schwarzenbach/Salle, Germany. Yet another suitable material for use as a substrate may have a basis weight of from about 50 grams/m$^2$ to about 60 grams/m$^2$ and have a 20/80 blend of viscose fibers and polypropylene fibers. The substrate may also be a 60/40 blend of pulp and viscose fibers.

The lotion of the present invention may comprise at least about 0.05% w/w of an anti-stick agent and at least about 0.01% of a performance enhancing agent. The lotion may comprise equal to or less than about 50% w/w of an anti-stick agent and equal to or less than about 3% of a performance enhancing agent.

Suitable water-soluble anti-stick agents to be used for the wipe include, but are not limited to:

Non-polymeric anti-stick agents such as glycerol and related polyols such as sorbitol, maltitol, xylitol, pentaerythritol, sucrose, glucose, maltose, maltotriose, maltodextrin, maltopentose, maltohexose, and isomaltulose, ethylene glycol, propylene glycol, butylene glycol, and the like, Polymeric anti-stick agents comprising polyethylene glycol, polypropylene glycol, polybutylene glycol, polyglycerol or mixtures thereof, including block copolymers comprising ethylene oxide and propylene oxide, and the like, Alkoxylated polyol compounds, and combinations of the above.

Method of Making an Absorbent Article Comprising the Lotion Composition of the Present Invention The lotion compositions of the present invention can be applied to the absorbent articles by any known or otherwise effective technique for distributing a lotion composition onto an absorbent product such as a disposable absorbent article. Nonlimiting examples of methods of applying the lotion compositions to an absorbent article include spraying, printing (e.g., flexographic printing), coating (e.g., contact slot coating and gravure coating), extrusion, or combinations of these application techniques. The application of the lotion compositions onto an absorbent article facilitates the transfer or migration of the lotion compositions onto the skin for administration and/or deposition of the lotion compositions, resulting in a safe and effective amount of the lotion compositions being applied. Therefore, the safe and effective amount of the lotion composition that will transfer or migrate to the body will depend on factors such as the type of lotion composition that is applied, the portion of the body facing surface where the lotion composition is applied, and the type of absorbent article used to administer the lotion composition.

Any suitable method can be used in determining the amount of a lotion composition described herein that is transferred to the body of a wearer during use of an absorbent article containing the lotion composition. Examples of methods for the calculation of transfer amounts of lotion compositions include Gas Chromatographic and other quantitative analytical procedures that involve the analysis of in vivo skin analog materials. A suitable Gas Chromatographic procedure is more fully described in WO 99/45973, Donald C. Roe et al, published Sep. 16, 1999.

In preparing absorbent articles according to the present invention, the lotion composition may be applied to a topsheet and/or to the leg cuffs and/or to the barrier cuffs as liquid or as a semi-liquid. Typically, the lotion composition is applied to the outer surface or outer surfaces that in use are in contact with the skin of the wearer, i.e. the lotion composition is applied to the body facing surface.

The lotion composition is typically applied from a melt thereof to the absorbent article topsheet and/or to the leg cuffs and/or to the barrier cuffs. Since the lotion composition may melt at above-ambient temperatures, it is usually applied as a heated lotion composition to the topsheet and/or to the leg cuffs and/or to the barrier cuffs. Typically, the lotion composition is heated to a temperature in the range from about 40° to about 100° C., from 50° or from 60° C. or even from to 90° C. to about 100° C., prior to being applied to the topsheet and/or to the leg cuffs and/or to the barrier cuffs. Typically, the liquid or semi-liquid components and/or the lotion composition is heated to ensure it is liquid or semi-liquid. Then, once the lotion composition has been applied to the topsheet and/or to the leg cuffs and/or to the barrier cuffs, it is allowed to cool and solidify to form solidified coating on the surface of the topsheet and/or to the leg cuffs and/or to the barrier cuffs.

The lotion composition can be applied uniformly or non-uniformly to the body facing surface of the article topsheet. By non-uniform it is meant here the amount, location, pattern of distribution of the lotion composition can vary over the topsheet surface. For example some portions of the treated surface of the topsheet and/or leg cuff and/or barrier cuff can have greater or lesser amounts of lotion composition (i.e. some portions comprise a higher basis weight of the lotion composition than other portions), including portions of the surface that do not have any lotion composition on it. In one embodiment, the surface of the topsheet and/or to the leg cuffs and/or to the barrier cuffs will have regions where no lotion composition is applied.

Where the lotion composition is applied non-uniformly, it can be applied intermittently, i.e. discontinuously. Any pattern may be utilized, including, for example, application of small droplets (obtained via, e.g., spraying) discrete figures, such as dots, rectangles (obtained via, e.g., gravure printing), alternating stripes that run in the longitudinal or lateral direction of the article, etc. By alternating stripes is meant regions in which the lotion is applied as stripes separated by regions which have no lotion composition applied.

The stripes may have a width from between 0.1 mm to about 50 mm, from between 0.1 to about 30 mm, from between 0.5 mm to about 50 mm, from about 0.5 mm to about 40 mm, from between 2 mm to about 40 mm, from between 2 mm to about 20 mm, from between 2 mm to about 15 mm, or from between 5 mm to about 20 mm. The spacing between the stripes having no lotion composition applied may have a width from between 0.1 mm to about 100 mm, from about 0.1 mm to about 50 mm, from between 0.1 to about 30 mm, from between 0.5 mm to about 50 mm, from about 0.5 mm to about 40 mm, from between 2 mm to about 40 mm, from between 2 mm to about 20 mm, from between 2 mm to about 15 mm, or from between 5 mm to about 20 mm. The substance can be applied directly to the absorbent article topsheet and/or leg cuff and/or barrier cuff or it may be applied to another material or component which is then adhered to the desired portion of the absorbent article (such as a calendar roll). For example, it may be applied in one or more longitudinal stripes. The stripes may go along the whole longitudinal length of the article or the stripes may only be present in the center zone of the topsheet or cuffs, e.g. the central 30%-70% of the surface area of the topsheet or cuffs.

The pattern, in which the lotion composition is applied and/or the amount of lotion composition applied can be the same for the rear third of the article (i.e. a third of the longitudinal extension of the absorbent articles starting from the outer edge of the chassis in the rear waist region), the central third of the article and the front third of the article. Alternatively, the pattern, in which the lotion composition is applied and/or the amount of lotion composition applied can be different for the rear, central and front third of the article.

As the lotion composition of the present invention has anti-stick properties, it should be comprised in those regions of the absorbent articles, which lie adjacent the skin areas of the wearer, which typically are contaminated with feces.

Thus, the lotion composition should at least be comprised in those regions of the articles, which lie adjacent the buttocks and the whole groove length of the wearer in use, also in the region of the genitals.

If the lotion composition is applied in the form of longitudinal stripes, the stripes may extend into the rear waist region of the absorbent article to the extent that they also cover the buttocks and most of the groove length. Also, the number or the density of the stripes may be higher in those areas lying against the areas typically affected with feces smeared against the skin. Further, the basis weight of the stripes may be higher in those areas lying against the areas typically affected with feces smeared against the skin.

If the lotion composition is applied in the form of figures, the density (i.e. dots lying closer together) and/or the size of the dots and/or the basis weight of the lotion composition comprised by the dots may be higher in those areas lying against the areas typically affected with feces smeared against the skin. The figures can have any shape and size such as round, oval, rectangular, triangular, star-shaped, heart-shaped or shaped in the form of an animal. Also, the absorbent article can comprise different shapes and/or different sizes.

The lotion compositions of the present invention may be prepared by any known or otherwise effective technique, suitable for providing a lotion composition comprising the essential skin treatment agents defined herein. The resultant lotion composition can subsequently be applied to a topsheet component of an absorbent article using a contact applicator such as a Nordsen EP 11-12-02.

The lotion compositions of the present invention are prepared such that the lotion compositions can be applied to an absorbent article to result in safe and effective amounts of the lotion compositions being transferred onto the skin of a wearer of the absorbent article. Therefore, the lotion compositions may have a product consistency such that they are relatively immobile and localized on the body facing surface of the absorbent article at ambient conditions, are readily transferable to the wearer at body temperature, and yet are not completely liquid under extreme storage conditions. In other words, the lotion compositions may be solids or semisolids at ambient conditions (about 25° C.) and/or body temperature (about 37° C.) so that the lotion compositions are easily transferred onto the skin by way of normal contact, wearer motion, and/or body heat. The consistency of the lotion compositions can be measured according to ASTM D5 test method which involves the use of a penetrometer to measure consistency. Typically, the lotion compositions of the present invention have a consistency of from about 10 millimeters (mm) to about 300 mm, from about 20 mm to about 250 mm, or from about 30 mm to about 200 mm, as measured at 40° C. according to the test procedure outlined in ASTM D5 test method.

The solid or semisolid consistency of the lotion compositions provide for relatively low levels of the lotion compositions to be applied to the absorbent articles to impart the desired lotion composition benefits. By "semisolid" is meant that the lotion compositions have a rheology typical of pseudoplastic or plastic liquids such that the lotion compositions remain relatively stationary in a desired location on the absorbent article, and do not have a tendency to flow or migrate to undesired locations of the article. Solid lotion compositions of the present invention likewise can remain in a particular location and not flow or migrate to undesired locations of the article. These solid and semisolid lotion compositions have viscosities high enough to keep the lotion compositions localized on an intended location of the article, but not so high as to impede transfer to the wearer's skin. Typically, final products of solid and semisolid lotion compositions have viscosities ranging from about $1.0 \times 10^6$ centipoise to about $1.0 \times 10^{10}$ centipoise under shear stress conditions of about $3 \times 10^3$ dynes/cm$^2$ at 40° C. (the shear stress applied to the lotion compositions while the absorbent article is in storage or transported at temperature conditions of about 40° C.).

However, the solid and semisolid lotion compositions can be made flowable for transfer or migration of the lotion compositions onto the skin by applying shear stress that results in deformation of the lotion compositions. A shear stress, which typically occurs at least once during wear of the absorbent article under temperature conditions of about 40° C. is typically at about $1.0 \times 10^6$ dynes/cm$^2$, and this shear stress can result in the lotion compositions having a viscosity of from about $1.0 \times 10^1$ centipoise to about $1.0 \times 10^5$ centipoise. It is believed that the lotion compositions achieve the lower viscosity values under applied shear stress due to the fact that, while the lotion compositions contain solid components, they also contain liquid materials. During wear of an absorbent article described herein, it is desirable to achieve a low viscosity for obtaining sufficient lubrication between the wearer's skin and the body contacting surface of the article to result in effective transfer of the lotion composition onto the wearer's skin. Viscosity at various shear stress can be measured using rheometers known in the art such as the Rheometer SR-2000 available from Rheometrics Incorporation.

Processes for assembling absorbent articles such as the disposable absorbent articles described herein include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031.

Test Methods

Skin Adherence (Anti-Stick)

This method may be used for assessing the adhesion of soils or exudates to the skin by quantifying the percentage of residual artificial pasty bowel movement ("ABM") left on the skin surface after treatment. The ABM, similar to real infant BM, fails cohesively, resulting in part of the ABM remaining on the skin surface and part of the ABM being removed. The more efficient the lotion composition is the lower is the percentage of residual ABM on the skin surface.

At least eight healthy adults participate in a single screening study. Each of the panelists completes a four-day washout period during which they use Olay® unscented moisturizing soap, as distributed by The Procter and Gamble Company, Cincinnati, Ohio, to wash their forearms. Panelists must refrain from using any topical product, such as ointments, creams or lotions, on their forearms during this washout-out period and also on the day of the screening study. On the day of testing, panelist's arms are inspected to ensure they are free of cuts, scratches, and rashes. If any skin abnormalities are present, the panelist cannot participate.

A template and a fine-tip marker are used to mark-off up to ten 3 cm by 3 cm sites on the hair-free volar forearms, i.e. up to ten sites per panelist with 5 sites per forearm. All but one of these sites is treated with a lotion composition. Thus, 9 different lotion compositions are tested per panelist. The remaining site receives no anti-stick treatment, i.e. serves as a negative control. The locations of the various treatments, including the no-treatment site, may be randomized among the sites on each panelist. Testing starts at the site closest to the elbow on the left arm and, as testing on each site is completed, progresses to the site closest to the wrist on the left arm, then to the site closest to the elbow on the right arm, and finally to the site closest to the wrist on the right arm. For each site that is treated, a predetermined amount of 300 µg/cm$^2$ of the lotion composition is applied in the center of the site with a powder-free finger cot, Catalog #56613-413 as available from VWR Scientific of West Chester, Pa. The applied lotion composition is then spread over the entire site (the boundary of which is defined by the marks made using the template) using the powder-free finger cot, by placing the finger cot on top of the agent or lotion composition and lightly rubbing the finger cot over the skin surface using several side-to-side and up-and-down movements for a total elapsed time of 10-15 seconds. Examining the site from an oblique angle, the person conducting the test needs to ensure that a uniform film has been formed over the entire area of the site. The film is left exposed to air, untouched, for approximately 1 minute prior to proceeding with the subsequent steps.

A 1 ml syringe, such as Catalog # BD-309628 as available from VWR Scientific of West Chester, Pa., that has been filled with room temperature ABM and is devoid of air bubbles, is placed onto a tared four-place analytical balance. The weight is recorded. The syringe with ABM is held over the center of the test site on the forearm, in reasonably close proximity to the skin surface, and approximately 0.2 ml of ABM is dispensed onto the skin by pressing the plunger and by watching the gradations on the syringe. The ABM should form a reasonably uniform, compact mound in the center of the test site. The syringe is re-weighed on the analytical balance, and the weight is recorded. The quantity of ABM that was delivered to the forearm is calculated by subtracting the second weight from the first.

A 4 cm×4 cm piece of weigh paper, Catalog #12578-201 as available from VWR Scientific of West Chester, Pa., is tared on the four place analytical balance, centered over the ABM mound on the forearm test site, and gently lowered onto the ABM using forceps. The weigh paper must not be touched with fingertips, as this may transfer oils onto its surface. Next, a 500 g bottle-shaped weight, such as Catalog #12766-518 as available from VWR Scientific of West Chester, Pa., that exerts approximately 0.5 psi of downward force is placed over the weigh paper such that the mound of ABM under the weigh paper is approximately centered under the weight. The weight may be gently held in place or balanced on the forearm by the panelist for 30 seconds. After 30 seconds have elapsed, two fingers are placed gently on either side of the weigh paper to hold it in place, and the 500 g weight is slowly lifted. Using a pair of forceps, the weigh paper is slowly and gently peeled from the test site. The forceps are placed at the lower right corner of the weigh paper, and the weigh paper is slowly peeled upwards in the direction of the upper left corner of the weigh paper. It should take approximately 1-2 seconds to remove the weigh paper. Once removed, the weigh paper is placed back onto the analytical balance that it was tared on, and the weight is recorded to determine the amount of ABM removed.

The above steps are repeated until all sites per panelist have been tested, i.e. the steps consisting of application of lotion composition, application of ABM, application of weigh paper, application of weight, and removal of weigh paper. For the no-treatment control, application of agent or lotion composition is skipped and ABM is applied directly to the skin site. The weight percent (%) residual ABM left on the skin surface after treatment is calculated from the weight measurements according to the equation $$((\text{ABM Applied} - \text{ABM Removed})/\text{ABM Applied}) \times 100.$$

The mean value for residual ABM and standard error of the mean for each lotion composition and for all panelists is calculated. When the method is run correctly, the no treatment control typically yields a value between approximately 30% to 35% residual ABM. To ensure reproducible results, the Anti-Stick Screening Method should be run at a room temperature of 21° C.±2° C. and at a relative humidity of 30-50%.

Preparation of Artificial Pasty Bowel Movement (ABM)

The following equipment is required:
an analytical balance accurate to ±0.001 g
a homogenizer capable of stirring the ingredients to homogeneity, such as an Ika Labortechnik™ T25 basic or equivalent as available from Ika-Werke GmbH and Co. KG of Staufen, Germany.
a homogenizer probe to be used with the homogenizer, such as Catalog # S25N 25F as available from Ika-Werke GmbH and Co. KG of Staufen, Germany.

The following reagents are required:
Feclone™ Powder #4, available from SiliClone Studio, Valley Forge, Pa., as Catalog Number Feclone BFPS-4.
Feclone™ Powder #6, available from SiliClone Studio, Valley Forge, Pa., as Catalog Number BFPS-6.
Feclone™ Powder #7, available from SiliClone Studio, Valley Forge, Pa., as Catalog Number BFPS-7.
Carbopol™ 981, available from BF Goodrich, Cleveland, Ohio
Deionized water.

The following quantities of the above reagents are required:

| Ingredient | Grams |
|---|---|
| Deionized water for Carbopol™ solution | 78.78 |
| Feclone™ powder #4 | 6.600 |
| Feclone™ powder #6 | 6.600 |
| Feclone™ powder #7 | 6.600 |
| Carbopol™ 981 | 0.900 |

The procedure to prepare the ABM consists of the following steps:

A. Preparation of Carbopol™ Solution
1. Weigh 78.78 g±0.01 g of deionized water in a 250 ml beaker.
2. Weigh 0.900 g±0.001 g of Carbopol™ on weigh paper.
3. Put beaker on a magnetic stirrer and set speed at 400 rpm.
4. Add Carbopol™ powder slowly to the water, over the span of about 5 minutes. While adding the Carbopol™, increase the stirring speed slowly to 600 rpm.
5. Once the Carbopol™ powder has been added to the water, cover the beaker and continue mixing at 600 rpm for 15 minutes. The Carbopol™ powder must be completely dispersed, i.e. a transparent gel without any agglomerates.
6. Set up a hot plate at 150° C. Place the Carbopol™ solution on the hot plate and continue mixing at 600 rpm until the solution is heated to 81° C. to 83° C.

B. Preparation of ABM Mixture
1. Weigh 6.600 g±0.01 g each of Feclone powders #4, #6, and #7 into a beaker and mix well.
2. Using a T25 basic or equivalent homogenizer with a homogenizer probe, stir the Carbopol™ solution at 8000 rpm for about 30 seconds before proceeding with Step 3.
3. To the Carbopol™ solution that is being stirred, slowly add the Feclone™ powder mixture, about one quarter of the total at a time. Ensure that the Feclone™ powder mixture gets pulled through the homogenizer probe during addition, i.e. is thoroughly mixed into the pasty lotion composition that is forming. If necessary, use a spatula to facilitate incorporation of the Feclone™ powder mixture into the lotion composition.
4. After all of the Feclone™ powder mixture has been added, continue mixing with the homogenizer at 8000 rpm for an additional 5 minutes, using the spatula to push the pasty lotion composition towards the homogenizer probe. The lotion composition should be thoroughly mixed and appear homogeneous.

The finished ABM may be placed in a container, such as Catalog #14233-954 as available from VWR Scientific of West Chester, Pa., and stored in the refrigerator for up to 30 days. After 30 days, a new sample should be prepared for further experiments. The container must be tightly sealed to avoid drying out of the ABM. Prior to using the ABM in the Anti-Stick Screening Method, the ABM must be removed from the refrigerator and allowed to adjust back to room temperature. An easy way to accomplish this is to fill a 10 ml syringe, such as Catalog # BD301604 as available from VWR Scientific of West Chester, Pa., with cold ABM and then allow the syringe to equilibrate to room temperature on a counter top. Equilibration typically takes about 15 minutes. The 10 ml syringe can then be used to fill the 1 ml syringe described in the Anti-Stick Screening Method.

EXAMPLES

The following example lotion compositions have been tested according to the skin adherence test method as described above with the ABM lotion composition as described above:

Example 1

Anti-Stick Lotion Composition

| 50 g | PEG 400 |
|---|---|
| 50 g | PEG 4000 |

The mean percentage of residual ABM for the lotion composition of example 1 as determined by the test method set out above has been 3%

Example 2

Anti-Stick Lotion Composition

| 50 g | BRIJ 700 (steareth-100) |
|---|---|
| 50 g | PEG 400 |

The mean percentage of residual ABM for the lotion composition of example 2 as determined by the test method set out above has been 3%

Example 3

Anti-Stick Lotion Composition

| 80 g | PEG 1000 |
|---|---|
| 5 g | PEG 4000 |
| 5 g | PEG 400 |

10 g Microthene FN51000 (made of polyethylene) available from Equistar Chemicals, Houston, Tex., USA.

The mean percentage of residual ABM for the lotion composition of example 3 as determined by the test method set out above has been 8%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claimed all such changes and modifications that are within the scope of this invention.

What is claimed is:

1. An absorbent article, intended to be worn by a wearer, wherein at least a part of a body facing surface of the article comprises a lotion composition, the lotion composition consisting of:
    a first compound which is liquid at 25° C.; and
    a second compound which is solid at 25° C.;
    wherein the first compound is a liquid polyethylene glycol and the second compound is a solid fatty compound selected from the group consisting of solid fatty acids, solid fatty alcohols and solid fatty soaps and wherein when the solid fatty compound is a solid fatty acid, then a total amount of liquids is higher than a total amount of solids.

2. The absorbent article of claim 1, wherein the article comprises on the body facing surface an effective amount of the lotion composition.

3. The absorbent article of claim 1, wherein the lotion composition is hydrophilic.

4. The absorbent article of claim 1, wherein the amount of the first compound is from about 3 wt. % to about 90 wt. % based on the total lotion composition; wherein the amount of the second compound is from about 10 wt. % to about 97 wt. % based on the total lotion composition and wherein the weight ratio of the first to second compound is from about 1:32 to about 9:1.

5. The absorbent article of claim 1, wherein the liquid polyethylene glycol has a molecular weight from about 100 Daltons to less than about 720 Daltons.

6. The absorbent article of claim 1, wherein the body facing surface comprises a non-woven fiber material.

7. The absorbent article of claim 1, wherein the absorbent article is selected from the group consisting of diapers, pant-like diaper, adult incontinence articles, tampons, interlabial device, sanitary napkins and panty-liners.

8. The absorbent article of claim 1, wherein the lotion composition is discontinuous in the form of a pattern of stripes or figures, and wherein the pattern is non-homogeneous over a longitudinal extension of the article.

9. The absorbent article of claim 1, wherein the absorbent article comprises a topsheet, and/or a pair of barrier cuffs, and/or a pair of leg cuffs, and wherein the lotion composition is applied to at least a part of a topsheet and/or a pair of leg cuffs, and/or a pair of barrier cuffs.

10. The absorbent article of claim 9, wherein the topsheet comprises an apertured topsheet.

11. The absorbent article of claim 1, wherein the second compound comprises a solid fatty acid.

12. The absorbent article of claim 11, wherein the solid fatty acid comprises a saturated fatty acid.

13. The absorbent article of claim 11, wherein the solid fatty acid comprises a linear saturated fatty acid.

14. The absorbent article of claim 1, wherein the second compound comprises a solid fatty alcohol.

15. The absorbent article of claim 14, wherein the second compound comprises a linear unsaturated 1-alkanol.

16. The absorbent article of claim 14, wherein the second compound comprises a linear unsaturated 1-alkanol with at least 12 carbon atoms.

17. The absorbent article of claim 1, wherein the second compound comprises a solid fatty soap.

18. The absorbent article of claim 17, wherein the solid fatty soap comprises a metallic soap comprises calcium and/or magnesium.

19. The absorbent article of claim 17, wherein the solid fatty soap is calcium stearate.

20. A package comprising:
    one or more absorbent articles of claim 1; and
    one or more wipes;
    wherein a ratio of absorbent articles to wipes is from about 1:1 to about 1:3 or from about 1:1 to about 1:2.

* * * * *